(12) United States Patent
Nam et al.

(10) Patent No.: US 8,022,051 B2
(45) Date of Patent: Sep. 20, 2011

(54) COMPOSITION FOR PROTECTION AND IMPROVEMENT OF SKIN, OR REINFORCING SKIN BARRIER FUNCTION COMPRISING PHOSPHATIDYLSERINE

(75) Inventors: Sang-June Nam, Seongnam (KR);
So-Young Chung, Yongin (KR);
Jeong-Jun Han, Yongin (KR);
Wang-Keun Choi, Hwasung (KR);
Chang-Seo Park, Gwacheon (KR);
Yun-Sik Kim, Gwanak-gu (KR);
Sang-Woo Cho, Seocho-gu (KR);
Young-Ho Lee, Gangnam-gu (KR);
Jin-Wook Kim, Yongin (KR); Ui-Chan Koh, Gangnam-gu (KR)

(73) Assignee: Doosan Corporation, Seoul (KR)

( * ) Notice: Subject to any disclaimer, the term of this patent is extended or adjusted under 35 U.S.C. 154(b) by 776 days.

(21) Appl. No.: 11/665,868

(22) PCT Filed: Oct. 20, 2005

(86) PCT No.: PCT/KR2005/003500
§ 371 (c)(1),
(2), (4) Date: Nov. 14, 2007

(87) PCT Pub. No.: WO2006/043788
PCT Pub. Date: Apr. 27, 2006

(65) Prior Publication Data
US 2008/0193394 A1 Aug. 14, 2008

(30) Foreign Application Priority Data
Oct. 20, 2004 (KR) .................. 10-2004-0084108
Mar. 8, 2005 (KR) .................. 10-2005-0019310

(51) Int. Cl.
*A61K 31/685* (2006.01)
*A61P 17/00* (2006.01)
*A61P 17/16* (2006.01)

(52) U.S. Cl. ............................ 514/114; 514/121

(58) Field of Classification Search .................. None
See application file for complete search history.

(56) References Cited

U.S. PATENT DOCUMENTS

| 4,464,400 A | 8/1984 | Kimura et al. |
| 4,963,527 A * | 10/1990 | Bombardelli et al. .......... 514/25 |
| 5,716,638 A | 2/1998 | Touitou |

FOREIGN PATENT DOCUMENTS

| FR | 2823440 A1 * | 10/2002 |
| JP | 08003072 A * | 1/1996 |
| JP | 11-255617 | 9/1999 |
| KR | 2004-0085820 | 10/2004 |

OTHER PUBLICATIONS

Hamanaka et al., "Human Epidermal Glucosylceramides are Major Precursors of Stratum Corneum Ceramides." The Society for Invesitgative Dermatology, Inc. (2002): p. 416-423.
Rogers et al., "Stratum Corneum Lipids: The Effect of Ageing and the Seasons." *Arch Dermatol Res* (1996): vol. 288, p. 765-770.
Michalik et al., "Impaired Skin Wound Healing in Peroxisome Proliferator—Activated Receptor (PPAR)α and PPAR β Mutant Mice." *The Journal of Cell Biology* 154(2001): vol. 154 No. 4 (2001), p. 799- 814.
Sheu et al., "Topical Peroxisome Proliferator Activated Receptor—α Activators Reduce Inflammation in Irritant and Allergic Contact Dermatitis Models." *The Society for Investigative Dermatology* (2001): p. 94-101.
Kippenberger et al., "Activators of peroxisome proliferator-activated receptors protect human skin from ultraviolet-B-light-induced inflammation," *J. Invest. Dermatol.* (2001) 117: 1430-1436.

* cited by examiner

*Primary Examiner* — Johann Richter
*Assistant Examiner* — Frank Choi
(74) *Attorney, Agent, or Firm* — Merchant & Gould P.C.

(57) ABSTRACT

Disclosed is a composition containing phosphatidylserine as an effective ingredient, and more particularly to a composition containing phosphatidylserine as an effective ingredient for protecting and improving a skin, reinforcing a skin barrier function, suppressing and alleviating an inflammatory response, treating and improving an atopic skin, activating PPAR-a promoting a differentiation of the skin, protecting the skin and preventing and improving skin aging and wrinkle. Accordingly, it is possible to protect and improve the skin from the injury due to the ultraviolet or the external stimulating material such as chemical material and to reinforce and strengthen the skin barrier function using the composition, thereby improving a general skin state.

20 Claims, 9 Drawing Sheets

COMPOSITION FOR PROTECTION AND IMPROVEMENT OF SKIN, OR REINFORCING SKIN BARRIER FUNCTION COMPRISING PHOSPHATIDYLSERINE

TECHNICAL FIELD

The present invention relates to a composition containing phosphatidylserine as an effective ingredient, and more particularly to a composition containing phosphatidylserine as an effective ingredient for protecting and improving a skin, reinforcing a skin barrier function, suppressing and alleviating an inflammatory response, treating and improving an atopic skin, promoting a differentiation of the skin, protecting the skin and preventing and improving skin aging and wrinkle.

BACKGROUND ART

The mammal skin comprises various kinds of cells, performs a variety of functions and includes diverse chemical compositions. A variety of lipids exist between the different skin layers in various concentrations. Specifically, the dermis of skin consists of fibroblasts that mainly produce collagen and other proteins and a small quantity of lipid. On the contrary, the epidermis includes keratinocytes that produce the lipid but does not substantially produce the collagen. The collagen produced by the fibroblasts endows the skin with an extension strength and the lipid produced by the keratinocytes forms an interruption layer between a living tissue and an external to perform a skin barrier function.

As lipid ingredients in the skin, there are phosphatidylserine, phosphatidylethanolamine, phosphatidylinositol, triglyceride, glucosylceramide, ceramide, cholesterol, cholesterol sulfate, free fatty acids and the like. Among them, phosphatidylserine, phosphatidylethanolamine, phosphatidylinositol and the like that are phospholipids are distributed in the dermis and the ceramide-based materials are mainly distributed in the epidermis. The distribution ratio of the compositions and the lipid amount contribute to a skin barrier maintenance homeostasis and provide a rapid restoration action against external physical and chemical injuries.

The epidermis lipid during the aging is generally reduced contrary to the otherwise epidermis tissue, so that the skin barrier function is decreased. In addition, an overall epidermis lipid is reduced to a degree of about 30% of the young people, but each content proportion of the lipids is maintained. This validates that the lipids of the skin keratin are produced through lipid biosynthesis and ceramide biosynthesis pathways. It has been reported that the lipids of the skin keratin are actually derived from the phospholipids and the free fatty acids of the dermis [Hamanaka et al., *J. Invsti. Dermatol.*, 119, pp 416-423, 2002]. It has been also known that the skin proceeds to an aging skin as the ratio of the free fatty acids is changed [Rogers et al., *Arch. Dermatol. Res.* 288, pp 765-770, 1996].

The phosphatidylserine is a kind of the lipids present in the nature and a material consisting of serine group, phosphate group, glycerol and two fatty acid groups connected each other. A weight of lecithin occupies about a half of a dry weight of a human brain. Most of lecithin forms a nerve cell membrane. The phosphatidylserine is a kind of lecithin derivatives that are important ingredients of the cell membrane and present particularly in plenty in the brain. It seems that the phosphatidylserine is deeply concerned with function expressions of the nerve cells, for example energy flow for a life-support activity in the nerve cell membrane and information transfer such as neurotransmitter discharge or synapse activity. However, although the phosphatidylserine is present in plenty in the brain of an animal, it is present less than a concentration of 0.1% in the origin except the brain of the animal, so that it is difficult to obtain the phosphatidylserine in a large quantity from natural raw materials.

It has been recently known peroxisome proliferators activated receptors (PPAR) existing in skin constituting cells on the whole. It has been clarified that the PPAR plays an important role in expressions of the barrier restoration and inflammation healing processes of the skin.

Specifically, the PPAR is a factor of regulating the energy homeostasis. It has been known that the PPAR is concerned with the skin state regulation such as permeability regulation of the skin barrier, epidermis layer multiplication inhibition, differentiation induction of the epidermis layer and the like through various mechanism. Due to the properties, the PPAR acts as a core regulator of diverse skin diseases such as psoriasis, wound healing and acnes due to hyperplasia of the epidermis layer as well as inflammation related skin diseases.

Accordingly, although it has not been much known a specified signal transfer of a material contributing to the skin homeostasis, it is attempted a specific research on functions of the phospholipids related to the PPAR which has been recently known. It is known that the PPAR has three subtypes. Among them, it has been clarified that PPAR-a has a possibility of a receptor of the phosphatidylserine [Michalik et. al., *The Journal of Cell Biology*, 154, pp 799-814, 2001].

In actual fact, it has been clarified that when clofibrate, WY14643 and the like, which are already known-agonists of the PPAR-a, are applied to the skin, the inflammation due to the skin stimulating material is decreased [Sheu et. al., *The Journal of Investigative Dermatology*, 118, pp 94-101, 2002].

Up to date, materials such as glucocorticoid have been used as anti-inflammatory agent. However, if continuous administration or treatment thereof is conducted, a chronic side-effect is caused, so that an immunological reaction is mainly decreased and thus the treatment is limited. Thereby, it has been considered that the agonist of the PPAR-a is a local and efficient treatment method, compared to the glucocorticoid (Sigma, USA).

In addition, the skin aging is classified into a photo-aging observed in the skin that is exposed to the ultraviolet for a long time and an intrinsic aging (chronological aging) observed in the skin that is not exposed to the ultraviolet. In the photo-aging and intrinsic aging, the skin becomes thin clinically and there occurs a wrinkle in the skin due to a decreased elasticity of the skin. It is thought that deficiency of the matrix protein, which is produced from the cell in the dermis, is a main cause of the wrinkle. Of the matrix protein in the skin, the collagen occupies 90% or more and the elastin occupies about 3~4%. In general, the wrinkles are closely related with the collagen reduction in the skin tissue and the expression increase of a matrix metalloproteinase (MMP) which is a kind of the protease, which are closely connected with an activity of the fibroblasts in the dermis tissue. Although there are many research results about the collagen reduction and the MMP increase due to the ultraviolet and mechanisms thereof, a correct mechanism thereof has not been known up to now. A mechanism that has been most known is an activation of AP-1 (activator protein) due to the ultraviolet and a competition of TGF-β/smad, which is important for the collagen synthesis, for p300. The AP-1 and smad binding element (SBE) require the p300 so as to act as transcription factors. Since an amount of the p300 existing in the cell is limited, if one transcription factor is activated, the other transcription factor is impeded. Accordingly, the activation of the AP-1 by the ultraviolet causes the expression of the MMP to be increased and thus the synthesis of the collagen is decreased due to the increase of the MMP. Thereby, it is expected that the increase of the collagen amount and the impediment of the MMP expression may suppress the skin aging.

DISCLOSURE

Technical Problem

Accordingly, the present invention has been made to solve the above problems.

During the research on the various efficacies of the phosphatidylserine, the inventors found that the phosphatidylserine activates the PPAR-a of the tissue cell in the skin, thus suppresses and alleviates the inflammatory response of the skin due to the ultraviolet and the chemical material, and promotes the differentiation of the skin keratinocyte. In addition, it was validated that the phosphatidylserine protects the skin keratinocyte from the ultraviolet or reactive oxygen species and is effective against the aging and wrinkles of the skin due to the ultraviolet.

An object of the invention is to provide a phosphatidylserine containing composition for protecting and improving a skin, reinforcing a skin barrier function, suppressing and alleviating an inflammatory response, treating and improving an atopic skin, activating PPAR-a, promoting a skin differentiation, protecting a skin and preventing and improving skin aging and wrinkle.

Technical Solution

In order to achieve the above objects, there is provided a composition containing phosphatidylserine as an effective ingredient for protecting and improving a skin.

In addition, according to the invention, there is provided a composition containing phosphatidylserine as an effective ingredient for reinforcing a skin barrier function.

Additionally, according to the invention, there is provided a composition containing phosphatidylserine as an effective ingredient for suppressing and alleviating an inflammatory response.

In addition, according to the invention, there is provided a composition containing phosphatidylserine as an effective ingredient for treating and improving an atopic skin.

Further, according to the invention, there is provided a composition containing phosphatidylserine as an effective ingredient for activating PPAR-a.

In addition, according to the invention, there is provided a composition containing phosphatidylserine as an effective ingredient for promoting a skin differentiation and protecting a skin.

In addition, according to the invention, there is provided a composition containing phosphatidylserine as an effective ingredient for preventing and improving skin aging and wrinkle.

In the composition for suppressing and alleviating an inflammatory response, the phosphatidylserine activates the PPAR-a to suppress and alleviate the inflammatory response due to an external stimulation of the skin.

In the composition for treating and improving an atopic skin, the phosphatidylserine reinforces a barrier function of the skin to treat and improve the atopic skin having a weak skin barrier function.

In the composition for promoting a differentiation of the skin and protecting the skin, the phosphatidylserine activates the PPAR-a to promote a differentiation of the skin keratinocyte.

In the composition for promoting a differentiation of the skin and protecting the skin, the phosphatidylserine protects the skin keratinocyte from the ultraviolet irradiation or reactive oxygen species.

In the composition for preventing and improving the skin aging and wrinkle, the skin aging and wrinkle result from the ultraviolet irradiation.

In the composition, the phosphatidylserine may be extracted from vegetable originated lecithin such as soybean and corn, animal oil and fat such as yolk and fish oil, a brain of an animal or milk, or manufactured by a phospholipase D transition reaction with the extracted lecithin.

In the composition, the phosphatidylserine may be hydrogenated phosphatidylserine.

The composition may further comprise oil and fat.

The composition may be used for trans-dermal administration or oral administration.

Advantageous Effects

According to the invention, since the phosphatidylserine activates the PPAR-a of the tissue cell in the skin, the phosphatidylserine containing composition has effects of suppressing and alleviating the inflammatory response of the skin due to the skin external stimulation, reinforcing the skin barrier function to treat and improve the atopic skin having a weak skin barrier function, activating the PPAR-a of the tissue cell in the skin to promote a differentiation of the skin keratinocyte, protecting the skin keratinocyte from the ultraviolet or reactive oxygen species to promote the differentiation of the skin and to protect the skin, and preventing and improving the skin aging and wrinkles due to the ultraviolet. Accordingly, it is possible to protect and improve the skin from the injury due to the ultraviolet or the external stimulating material such as chemical material and to reinforce and strengthen the skin barrier function using the composition, thereby improving a general skin state.

BEST MODE

Figure 1:
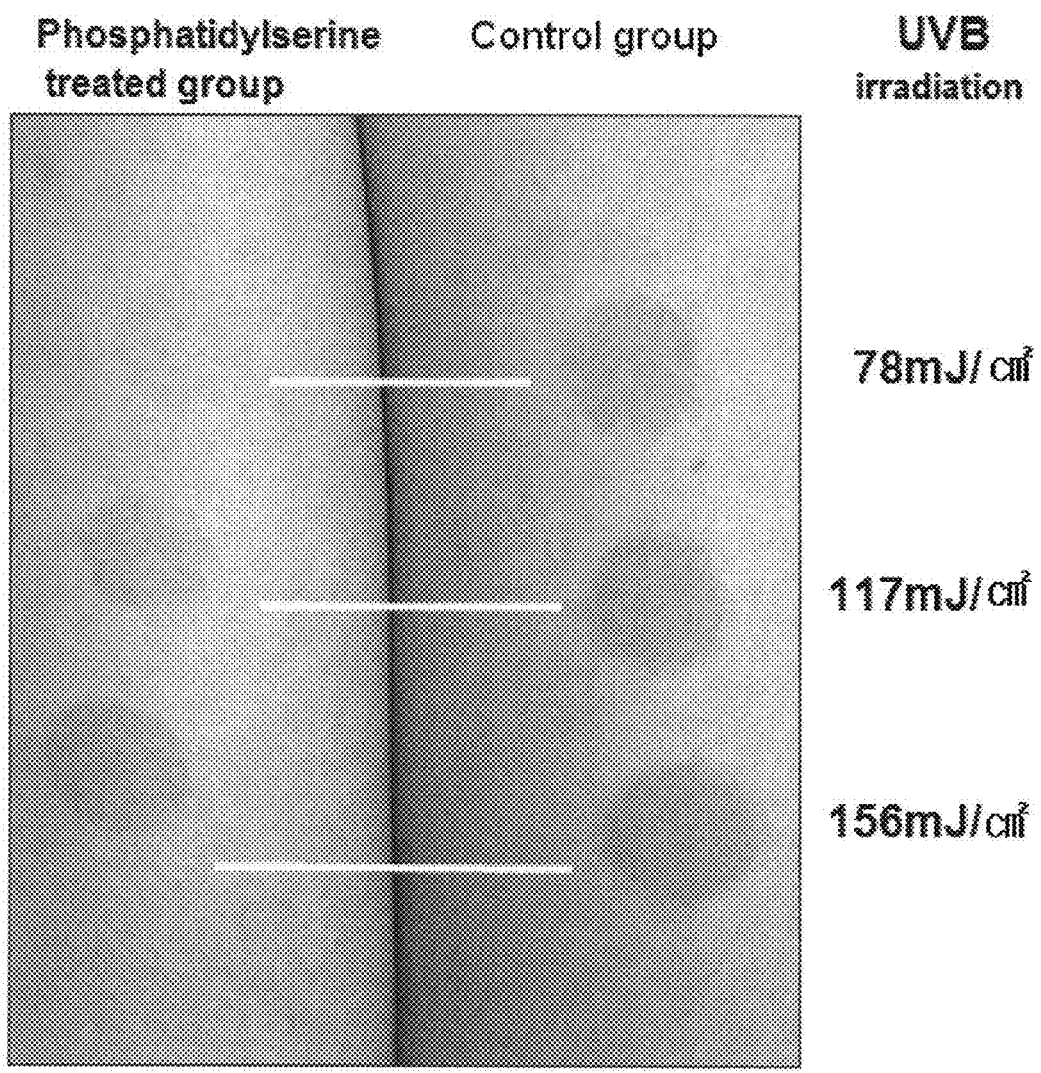
FIG. 1 shows a measurement result of a skin damage (inflammatory response)-alleviating effect of phosphatidylserine, which damage results from the ultraviolet irradiation.

Hereinafter, a preferred embodiment of the present invention will be described.

A composition of the invention may be a pharmaceutical composition. The pharmaceutical composition of the invention may be administrated in manners of oral, parenteral, rectal, vaginal, local, trans-dermal, intravenous, intra-muscular, intra-peritoneal, and subcutaneous administrations. The most preferred administration routes are oral and trans-dermal administrations. A dosage of a reactive compound may be different in accordance with treatment targets, specific diseases to be treated or pathological state, serious degrees of diseases or pathological states, administration routes and judgments of prescribers. A determination of the dosage based on the factors is within those skilled in the art. In general, the dosage is within a range of about 0.001 mg/kg/day~about 1000 mg/kg/day. A preferred dosage is 0.5 mg/kg/day~10 mg/kg/day.

The pharmaceutical composition of the invention may be formulated together with pharmaceutically acceptable carriers. It is disclosed a typical carrier and a method of manufacturing a typical pharmaceutical composition capable of being used for the invention in a reference material [Remington's Pharmaceutical Sciences, latest edition, by E. W. Martin (Merck Publ. Co., Easton, Pa.)]. The compound of the invention can be administrated together with other medicaments. In addition, the pharmaceutical composition of the invention can be administrated together with the other compositions and processes for the disease treatment. For example, a surgical operation, laser or chemical treatment can be simultaneously performed with the administration of the pharmaceutical composition of the invention.

In accordance with the intended administration types, the pharmaceutical composition may be administrated in a solid, semisolid or liquid form. The administration type includes tablet, capsule, suppository, small bag, granule, powder, cream, lotion, ointment, sticking plaster, liquid solution, suspension, dispersion solution, emulsion, syrup and the like, but is not limited thereto. A reactive ingredient may be capsulated in a liposome, micro particle, micro capsule or the like. However, the most preferred formulation is a trans-dermal administration formulation such as cream, lotion, ointment, liquid solution, suspension, dispersion solution, emulsion or the like.

In addition, the composition of the invention may be a functional cosmetic composition. The formulation of the cosmetic composition includes softening lotion, astringent lotion, lotion, cream, essence, capsule, powder and the like. The cosmetics may be formulated into a variety of forms according to the conventional methods.

In addition, the invention provides health functional foods including the compound and sitologically acceptable food supplementary additives. The foods to which the compound can be added include various foods, beverage, gum, tea, vitamin complex, health functional food and the like.

At this time, an amount of the compound in the food or beverage may be 0.001~99 wt. % based on the total food weight, and the health beverage composition may be added in a ratio of 0.001~0.1 g, preferably 0.05~0.1 g, based on 100 ml.

The health functional beverage composition includes the compound as an essential ingredient in the above-mentioned ratio and may contain a variety of flavorings, natural carbohydrates or the like as additional ingredients, as typical beverages, without specific limitations of other ingredients.

In addition, the composition of the invention may contain a variety of nutrients, vitamin, mineral (electrolyte), synthesized flavoring agent or natural flavoring agent, coloring agent and enhancer (cheese, chocolate and the like), pectic acid and salts thereof, alginic acid and salts thereof, organic acids, protective colloid thickening agent, pH modifier, stabilizer, antiseptics, glycerin, alcohol, carbonating agent for carbonated beverages and the like. In addition, the composition of the invention may contain flesh of fruit for manufacturing natural fruit juices, fruit juice beverages and vegetable beverages. These ingredients may be used in an independent or combination form. The ratio of the additives is not very important, but is generally within a range of 0 about 20 weight parts per 100 weight parts of the composition of the invention.

In the mean time, since the phosphatidylserine of the invention does not have severe toxicity and side effects, it can be safely used for a prevention purpose for a long time.

MODE FOR INVENTION

Hereinafter, the invention will be more specifically described with reference to preferred embodiments. However, it should be noted that the invention is not limited thereto.

Example 1

A Suppression Experiment of Skin Damage (Inflammatory Response) Due to the Ultraviolet Irradiation In order to examine a skin damage (inflammatory response)-alleviating effect of the phosphatidylserine of the invention, which stimulation results from the ultraviolet irradiation, a following experiment was performed. At this time, the skin stimulation (inflammatory response) due to the ultraviolet irradiation was measured with an erythema formation level.

First, it was measured minimal erythema dosage (MED) in arm inside parts of examinees (28 years old or more, 10 women and men, respectively). An aqueous solution including phosphatidylserine 0.5% (aqueous solution phase containing 5% PEG 300; PEG300, Sigma, US) was previously applied to the arm inside parts of the examinees in an amount of 30 µl which were then irradiated with UVB (Sankyo Denki G15T8E sunlamps UV-B, Japan) in an intensity of 2 MED (78 mj/cm$^2$), 3 MED (117 mj/cm$^2$) and 4 MED (156 mj/cm$^2$) to measure suppression degrees of the erythema formation. At this time, a group for which the phosphatidylserine was not treated was used as a control group.

As a measurement result, as shown in FIG. 1, the erythema formation was considerably suppressed in the phosphatidylserine-treated group, compared to the control group.

Example 2

An Alleviation Experiment of Skin Damage (Inflammatory Response) Due to 12-O-Tetradecanoylphorbol-13-Acetate (TPA)

In order to examine a skin damage (inflammatory response)-alleviating effect of the phosphatidylserine of the invention, which damage results from skin inflammation-inducing material, a following experiment was performed in accordance with a method used by Sheu et. al. (*The Journal of Investigate Dermatology*, 118, pp 94-101, 2002).

First, CD-1 mouse (male & female, 6-8 weeks, Charles River, US) was used as an experimental object. TPA (12-0-tetradecanoylphorbol-13-acetate) 0.03% (wt./vol.; in acetone) solution 10 µl, which was skin inflammation-inducing material, was treated to inner and outer parts of both ears of the experimental animal. The ear was thickened due to TPA and there occurred an inflammatory response. Then, clofibrate (1 mM) and Wy14643 (1 mM) as already-known positive control group, which are agonists of PPAR-a, and the 0.5% phosphatidylserine containing aqueous solution used as the Example 1 as an experimental material were applied to both ears in an amount of 30 µl per $cm^2$ at times of 45 minutes and 4 hours after the inflammation was induced. After that, the treated parts of the ears were subject to a biopsy, and the biopsy parts were fixed to 4% formaldehyde and then subject to Hematoxylene & Eosin (E&H) staining. The tissue slide stained with H&E was magnified to 100 folds to check the inflammation alleviation.

Figure 2:
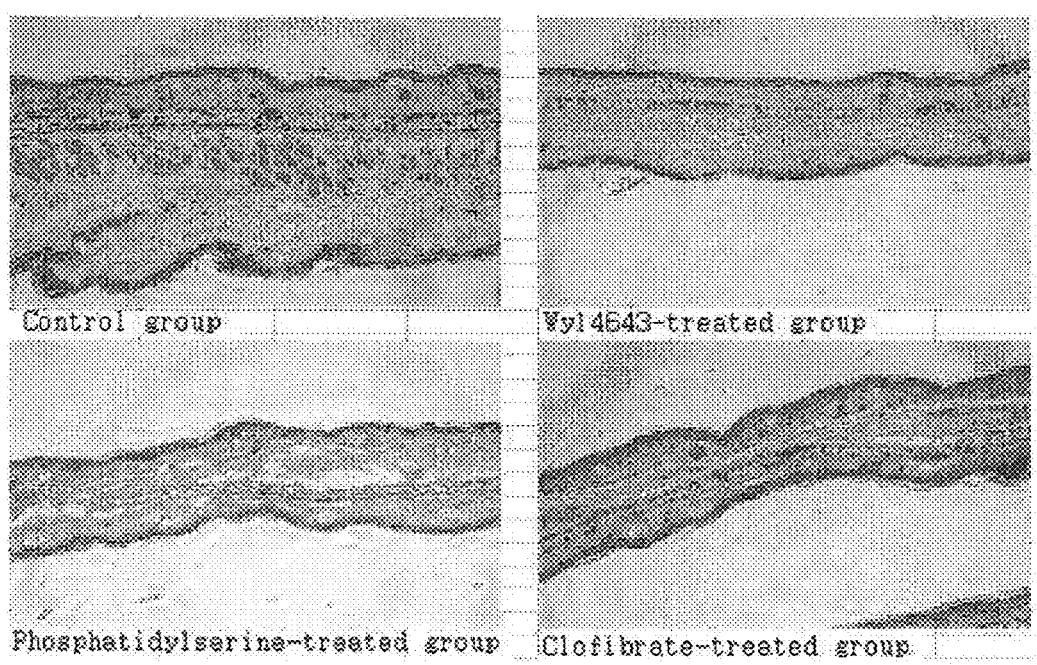
FIG. 2 shows a measurement result of a skin damage (inflammatory response)-alleviating effect of phosphatidylserine, which damage results from 12-O-tetradecanoylphorbol-13-acetate (TPA).

As a result of that, as shown in FIG. 2, it was validated that the tissue was considerably swelled in the control group (TPA only-treated), whereas the inflammation was alleviated in the phosphatidylserine-treated group. In addition, it was validated that the inflammation was alleviated in the clofibrate-treated group and the Wy14643-treated group c, which are agonists of PPAR-a and the positive control group.

Example 3

A Reduction Experiment of Inflammatory Response Induced by Ultraviolet Irradiation in the Skin Keratinocyte In order to examine an inflammatory response-reducing effect of the phosphatidylserine of the invention in the skin keratinocyte, which response results from the ultraviolet irradiation, a following experiment was performed in accordance with a method disclosed in the literature (Stefan et. al., *The Journal of Investigate Dermatology*, 117, pp 1430-1436, 2001).

First, the skin keratinocyte cell line (HaCaT, a gift from Yonsei univeritym, Korea) was seeded to a 35 $mm^2$ of cell culture dish in an amount of $3\times10^5$ cells/dish and then cultured for a day. Next day, the culture medium was removed and the cell was washed with 1× phosphate-buffered saline (PBS), 700 µl of 1×PBS was added to each of the dishes, it was irradiated 25 $mJ/cm^2$ UVB and then PBS was removed. The DMEM culture medium (Hyclone, USA) containing 20 µM and 40 µM of phosphatidylserine aqueous solution (DS-PS; Doosan R&D center, Korea) and 200 µM of WY-14643 (Sigma, USA) (positive control group) added thereto was added and then cultured 24 hours. Next day, the culture medium was collected and then amounts of TNF-a and IL-6 which have been known as inflammatory cytokines were measured with an enzyme-linked immunosorbent assay (ELISA) method. In addition, in order to check that there occurred a similar inflammatory response reducing effect also in the normal human skin keratinocyte, an experiment was performed in the above-mentioned manner using normal human keratinocytes (a gift from Dong-guk University) instead of the HaCaT cell line and then an amount of IL-1alpha secreted to the culture medium was measured with the ELISA. The result is shown in FIG. 3.

Figure 3:
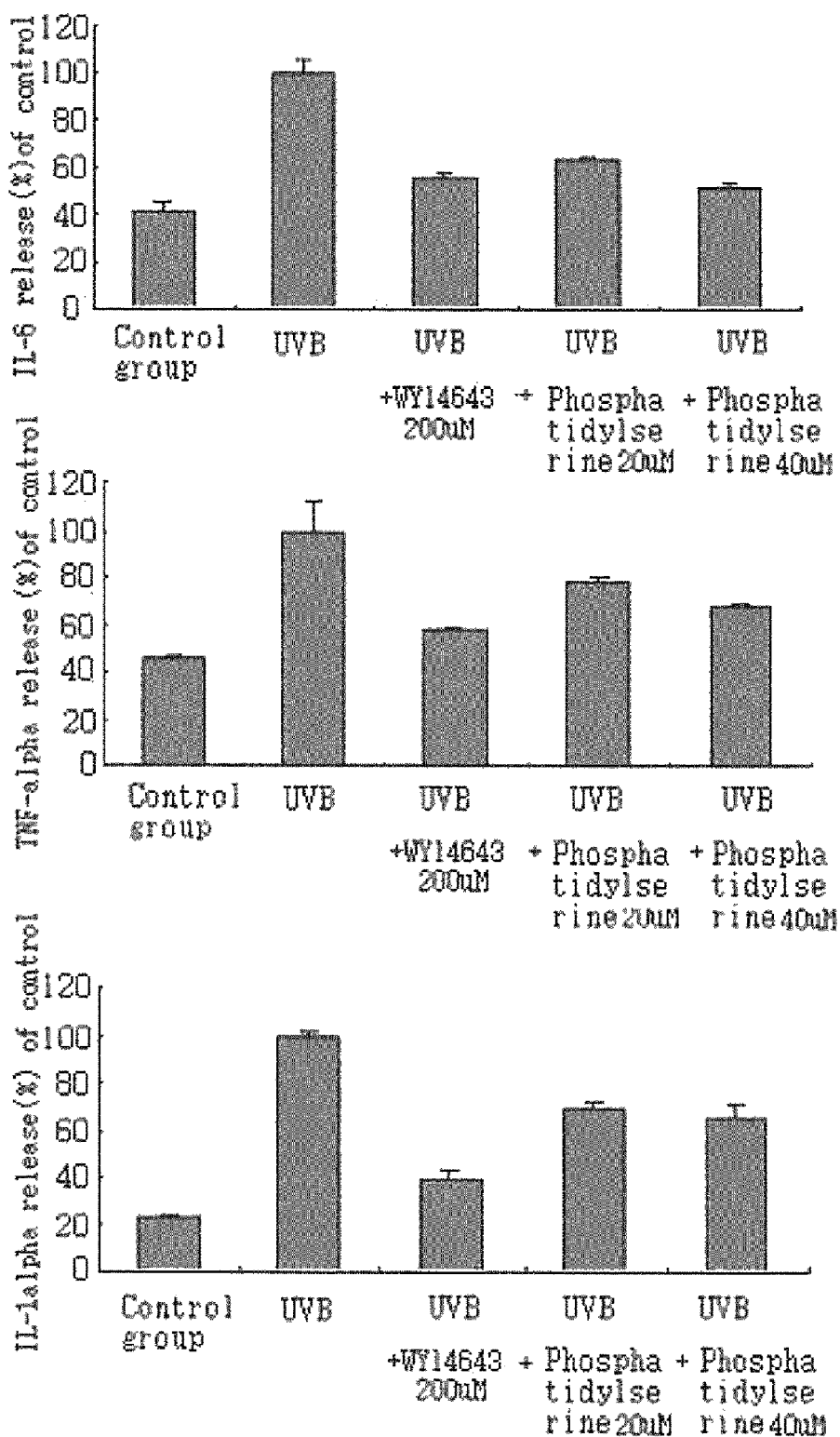
FIG. 3 is a graph showing a measurement result of skin keratinocyte damage-alleviating and inflammatory response-suppressing effects of phosphatidylserine, which damage and response result from the ultraviolet irradiation.

As can be seen from FIG. 3, it was validated that the inflammatory response increased due to the ultraviolet irradiation in the skin keratinocytes was considerably alleviated in the phosphatidylserine-treated group, as the WY14643-treated group which was the positive control group.

Example 4

A Protection Experiment of the Skin Keratinocyte from the Ultraviolet Injury

In order to examine a keratinocyte protecting effect of the phosphatidylserine of the invention from the ultraviolet injury, a same experiment as the example 3 was performed. Last day, the cell was photographed with a digital camera attached to a microscope and a cell survival was checked with a 3-(4,5-dimethylthiazol-2-yl)-2,5-diphenyltetrazolium bromide (MTT) assay.

Figure 4:
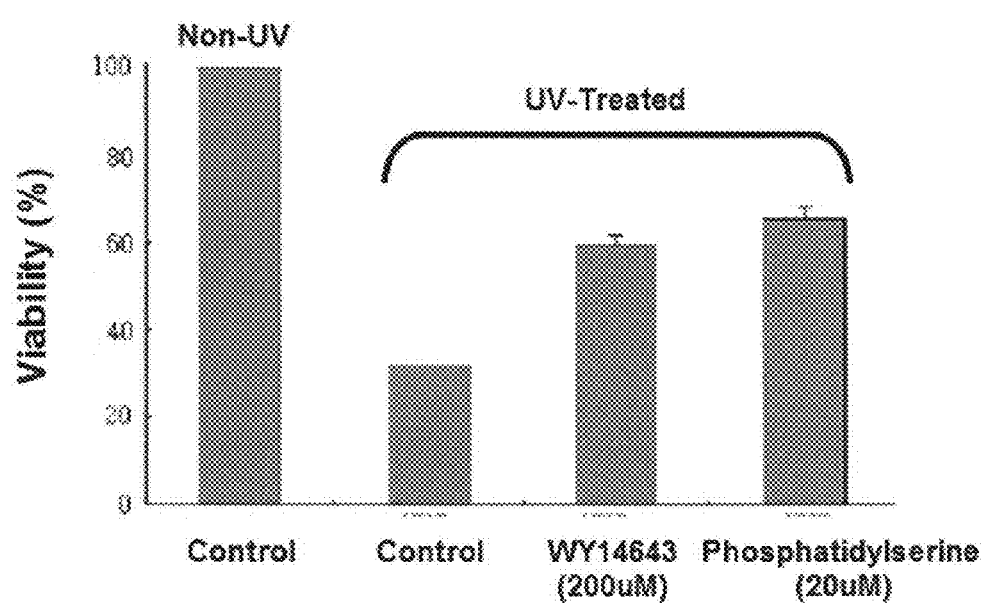
FIG. 4 is a graph showing a measurement result of a skin keratinocyte protecting effect of phosphatidylserine with regard to the ultraviolet injury.

As a result of that, as shown in FIG. 4, it was validated that the phosphatidylserine protected the skin keratinocytes from the ultraviolet injury, similarly to the WY14643 which was the known agonist of PPAR-a.

Example 5

An Observation of a Differentiation Promoting Effect in the Skin Keratinocytes

In order to examine a differentiation promoting effect in the skin keratinocytes by the phosphatidylserine of the invention, a following experiment was performed.

First, the normal human keratinocytes (a gift from Dong-guk University) cultured in the KSFM (Keratinocyte-SFM; Gibco BRL/Life Technologies, USA) were seeded to the 35 $mm^2$ cell culture dish in an amount of $1.5\times10^5$ cells/dish and then cultured for a day. Next day, the culture medium was removed and a new culture medium containing 20 and 40 µM of phosphatidylserine aqueous solution, 1.2 mM calcium aqueous solution and 200 and 400 µM of clofibrate (Sigma, USA) added thereto was added and cultured for 24 hours. Next day, in order to make sure of a differentiation of the keratinocyte, a morphology change of the cell was checked with a phase contrast microscope (Nikon, Japan) and a photograph was taken with a digital camera attached to the microscope.

In addition, a western blot was performed to check the protein expression amount of involucrin and transglutaminase, which have been known as a differentiation-marker proteins of the keratinocyte peculiar to the keratin. 500 µl of a lysis buffer having 2% sodium dodecyl sulfate (SDS) added thereto wad added and the cells were collected with a cell scrapper, so that cell lysate only was obtained. A prepared western sample was subject to running to a 7.5% gel and transferred to a membrane, so that proper primary antibody and secondary antibody were attached and then a protein band was finally checked.

Figure 5:
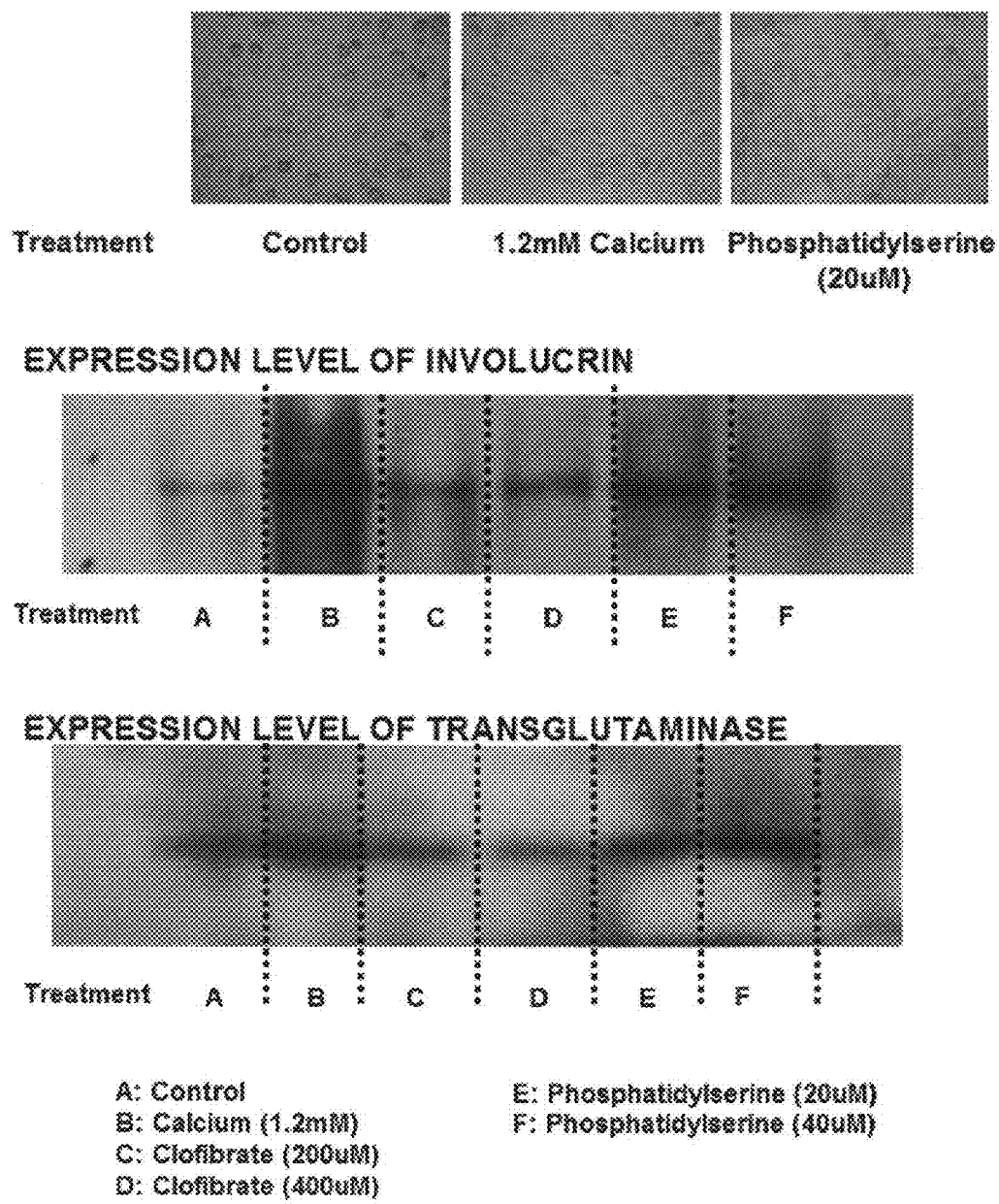
FIG. 5 shows a measurement result of a differentiation-promoting effect of phosphatidylserine in a skin keratinocyte.

As a result of that, as shown in FIG. 5, a high concentration calcium caused the expressions of the two proteins to be increased, and the clofibrate, which is the already-known PPAR-a agonist, also increased the expressions of the two proteins. The phosphatidylserine also rapidly increased the expressions of the proteins and an amount thereof was increased dependently on the concentration.

Example 6

An Experiment of Skin Differentiation Promotion in the Mouse

In order to examine a differentiation promotion of the skin in a mouse model, a following experiment was performed.

First, 0.5% phosphatidylserine aqueous solution was applied to the skin of a back region of the mouse (CD-1 mouse, male&female, 6-8 weeks, Charles River, USA) in an amount of 50 µl two times per a day for two weeks. After that, the skin tissue of the treated region was subject to the biopsy and then the biopsy tissue was fixed to 4% formaldehyde and sliced. Then, antibodies for involucrin and loricrin were attached and an expression amount of the protein was examined.

Figure 6:
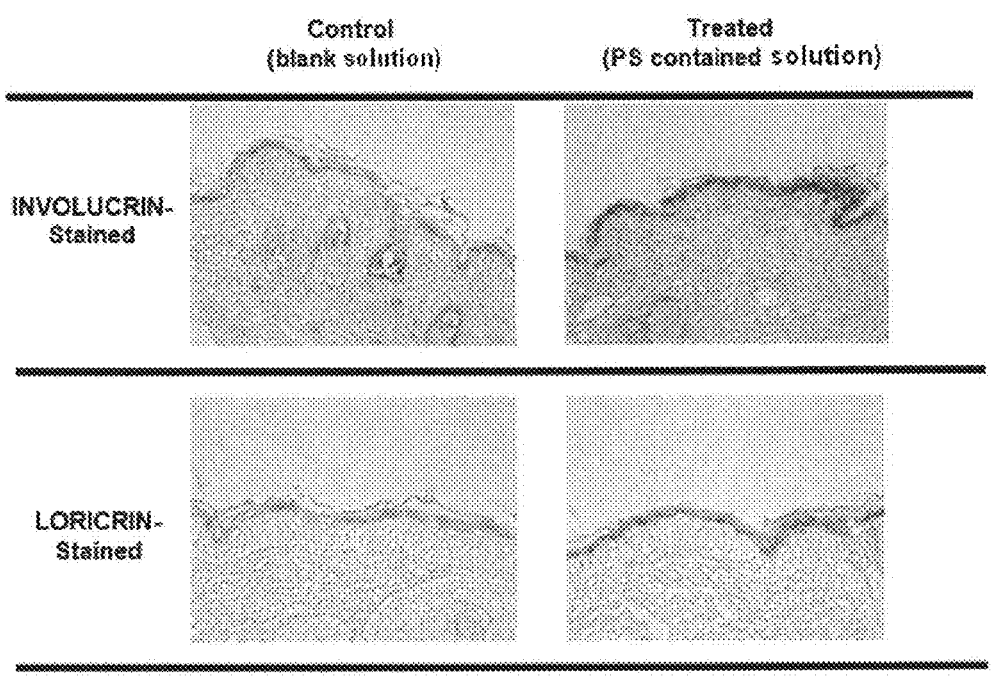
FIG. 6 shows a measurement result of a skin differentiation-promoting effect of phosphatidylserine in a mouse.

As a result of that, as shown in FIG. 6, compared to a negative control group (blank group), the expression amounts of the two proteins were remarkably increased in the group to which the 0.5% phosphatidylserine was applied.

Example 7

An Activation Experiment of PPAR-a in a HeLa Cell Line

In order to examine a PPAR-a activating effect of the phosphatidylserine of the invention, a following experiment was performed. At this time, it was examined activities for the PPAR-a and PPAR-γ retained.

First, a HeLa (Human epithelial carcinoma) (KCLB [Korean Cell Line Bank] No. 10002, Korea) was seeded to a 24-well plate in an amount of $2 \times 10^4$ cells/well and then cultured for a day. Next day, in order to perform a cell transfection, 200 ng of PPAR-a over-expression vector, 200 ng of PPRE (peculiar to PPAR-a)-luciferase reporter vector (Promega, USA), and 40 ng of renilla luciferase vector used as the control group in the cell (internal control, i.e., used to examine an transfection efficiency) were mixed in the OMEM (Gibco, USA) culture medium and subject to the transfection to the cell using the lipofectamin (Invitrogen, USA). After four hours, the culture medium was added to be 10% FBS and then cultured for one night. Next day, in order to measure an activity of PPAR-a, it was treated with 20 and 40 µM of phosphatidylserine and 400 µM of the clofibrate as the positive control group and then cultured for eight hours. An activity of the luciferase was measured with a luminometer using a dual luciferase assay system (Promega, USA). Also in case of PPAR-γ, the same process was performed to measure the activity. At this time, in case of measuring the activity of PPAR-γ, 10 and 50 µM of phosphatidylserine and 50 µM of cyglitazone (Sigma, USA) as the positive control group were treated. A measurement result of the activity of PPAR-a is shown in a first graph and a measurement result of the activity of PPAR-γ is shown in a second graph.

Figure 7:
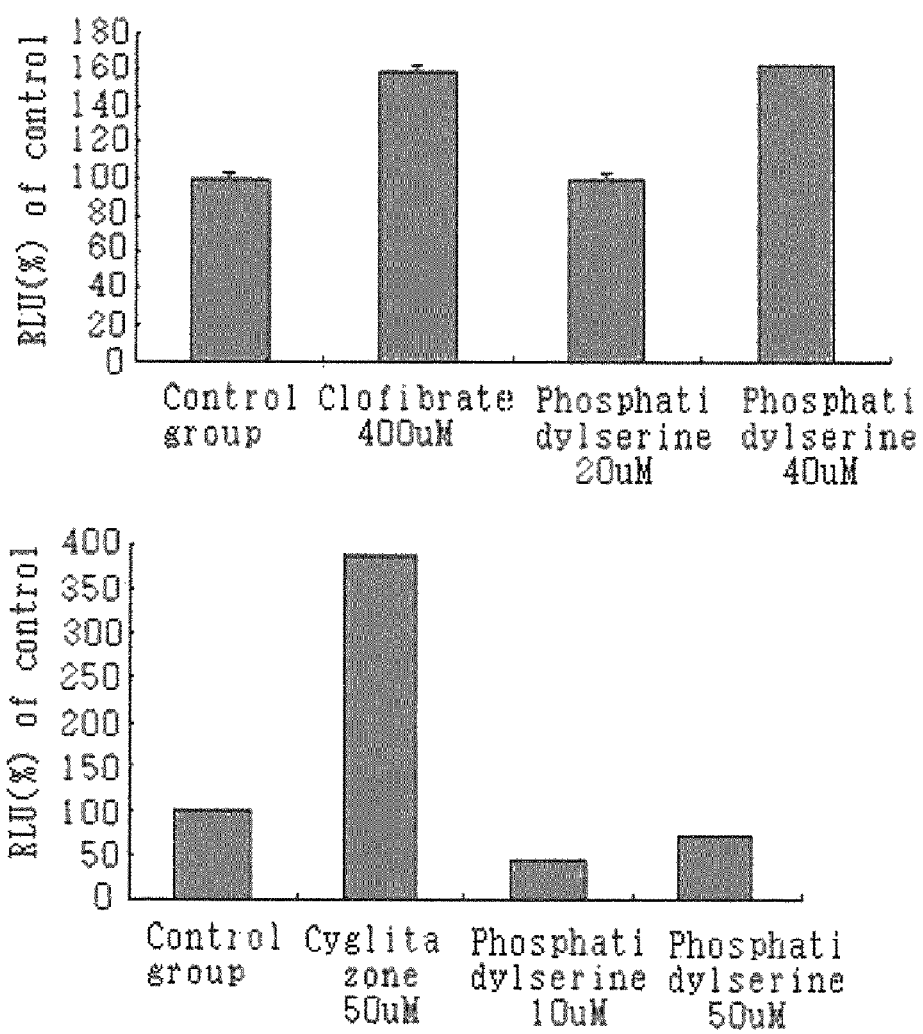
FIG. 7 shows a PPAR-a activating effect of phosphatidylserine.

As can be seen from FIG. 7, the phosphatidylserine activated the PPAR-a but had no influence on the PPAR-γ.

Example 8

A Measurement of a Skin Protection Effect from ROS in the Skin Keratinocyte

In order to measure an effect of protecting the skin from the ROS in the keratinocyte by the phosphatidylserine of the invention, a following experiment was performed.

First, the skin keratinocytes (HaCaT) were seeded to the 24-well plate in an amount of $5 \times 10^4$ cells/well. Next day, it was treated with 25 µM phosphatidylserine aqueous solution (Doosan Biotech, Korea) (phosphatidylserine-treated group), 100 µM vitamin C (ascorbic acid-treated group) and 100 µM vitamin E (a-tocopherol-treated group) as the positive control group and then cultured for 24 hours. Next day, it was treated with 1 mM hydrogen peroxide ($H_2O_2$) and then cultured for about 1~1.5 hours. Then, a cell viability was examined with the MTT assay.

Figure 8:
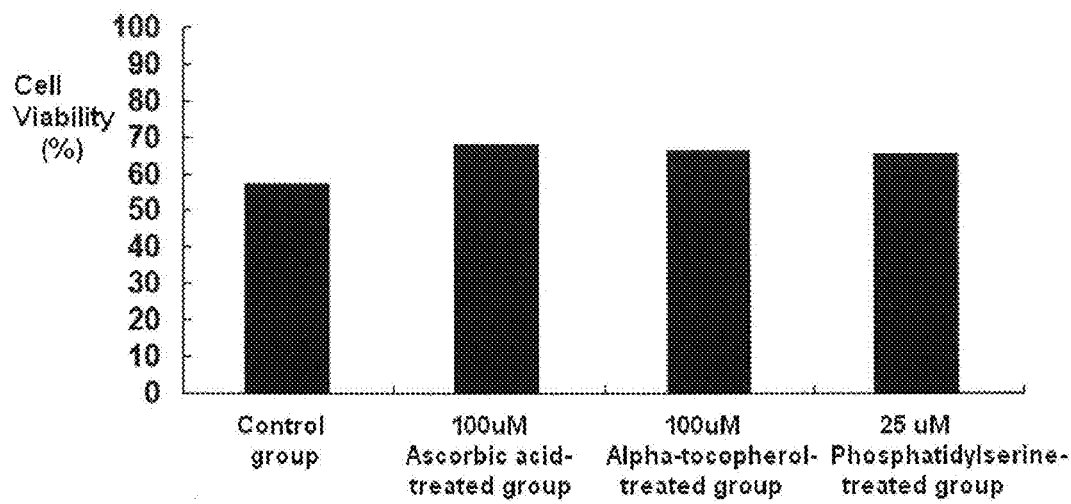
FIG. 8 is a graph showing a measurement result of a skin keratinocyte protecting effect of phosphatidylserine from reactive oxygen species (ROS) in a skin keratinocyte.

As a result of that, as shown in FIG. 8, it was validated that all the phosphatidylserine-treated group, the ascorbic acid-treated group and the a-tocopherol-treated group exhibited the protection effect from the reactive oxygen species. Among them, the phosphatidylserine exhibited the same protection effect with a smaller amount than the positive control material. From this, it could be seen that the phosphatidylserine protected the skin keratinocytes and thus the skin from the reactive oxygen species.

Example 9

A Skin Barrier Function Restoration-Reinforcing Effect of the Phosphatidylserine In this example 9, it was examined a difference of water loss restoration rates in a group to which the phosphatidylserine was administrated and a group to which the phosphatidylserine was not administrated, using the hairless mouse, so as to examine an effect of the phosphatidylserine on the skin barrier function restoring reinforcement.

First, a solution in which the phosphatidylserine (DS-PS, Doosan, Korea) was dispersed in a tertiary distilled water in a concentration of 400 mg/100 ml was used as a test material. It was prepared 10 hairless induced mice which were 8-42 weeks (Japan SLC Inc., Shizuoka, Japan). The solution was orally administrated to 5 mice of them in a dosage of 0.8 mg phosphatidylserine/mouse once a day and the tertiary distilled water was orally administrated to the other 5 mice. The medication period was three weeks. After that, it was measured a water evaporation loss for both sides of the backs of the hairless mice using a TEWL apparatus (TEWAMETER, TW210, Germany) (normal skin: about $10 \pm 2$ g/hm$^2$). A Scotch tape was attached to the same positions and then cleared. This was repeated about 15~20 times until the water evaporation loss reached 40~50 g/hm$^2$. After that, it was measured the water evaporation losses as time went by (i.e., before the injury, immediately after the injury, after 6 hours, after 9 hours and after 24 hours) to check the restoration rate of the skin barrier. The result is shown in FIG. 9.

Figure 9:
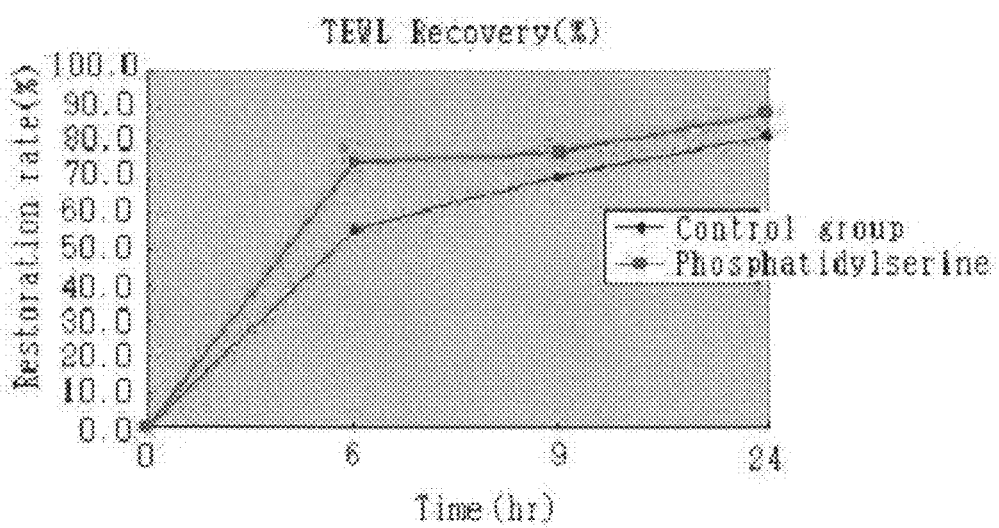
FIG. 9 is an experimental result proving a skin barrier function-reinforcing effect of phosphatidylserine through an oral administration, which shows a trans-epidermal water loss (TEWL) restoration rate as time goes by after injuring epidermis of a rat skin that is not given with phosphatidylserine for three weeks and a rat that is given with phosphatidylserine for three weeks.

As can be seen from FIG. 9, the mouse having taken the phosphatidylserine exhibited the higher restoration rate of the skin barrier function, compared to the mouse having not taken the phosphatidylserine. Accordingly, it could be seen that the phosphatidylserine exhibited an effect of reinforcing the skin barrier function.

Example 10

A Measurement of Expression Level of Pro-Collagen and Matrix Metalloproteinase by the Phosphatidylserine In order to examine a skin aging-suppressing efficacy of the phosphatidylserine of the invention, it was quantitatively measured the expression amounts of the pro-collagen and the matrix metalloproteinase (MMP). It was tried a protein-antibody reaction through an electrophoresis (western blot) as the quantitative method. The cultivation was performed in manners of irradiating the ultraviolet to the fibroblasts (a gift from Seoul National University, Korea) and otherwise. After that, it was treated with the phosphatidylserine (20 μM), the cell was collected to extract the protein parts. The extracted protein was dissolved in the sodium dodecyl sulfate (SDS) and then subject to the electrophoresis on the SDS-polyacrylamide gel. The protein in the gel after the electrophoresis was moved to nitrocellulose and reacted as an antibody of the pro-collagen and MMP-1 (collagenase) to exhibit a color. An amount of the protein was measured using the color.

Figure 10:
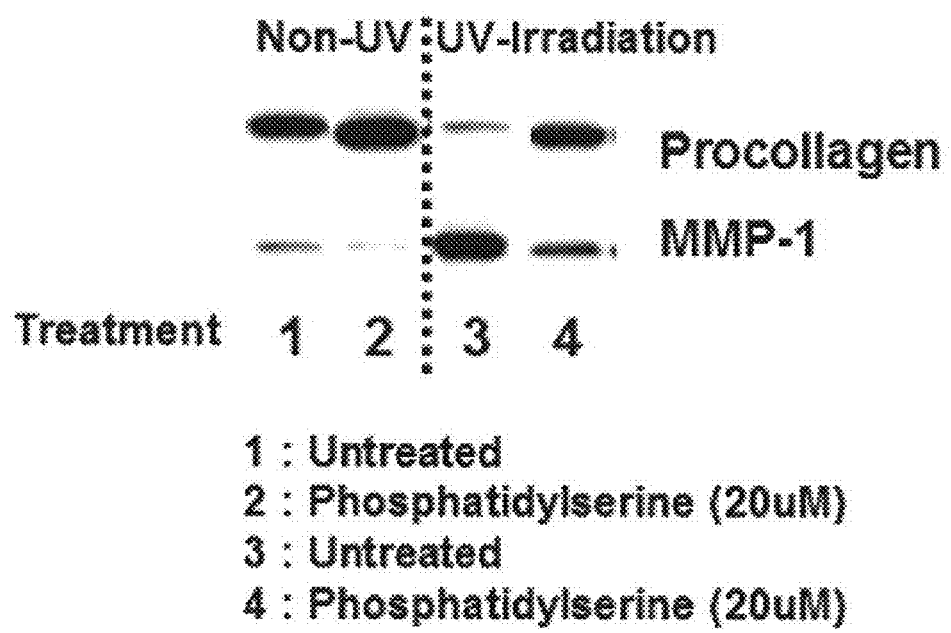
FIG. 10 shows a measurement result of increasing of a pro-collagen and a matrix metalloproteinase by phosphatidylserine.

As a result of that, as shown in FIG. 10, the phosphatidylserine increased the pro-collagen in both cases of the ultraviolet irradiation and otherwise, and decreased the expression amount of the MMP-1. Accordingly, it was validated that the phosphatidylserine performed the function of suppressing the skin aging.

Hereinafter, formulation examples of the composition will be described. However, it should be noted that the examples are given to illustrate the invention, not to limit the invention.

| Formulation example 1: Soap | |
| --- | --- |
| Phosphatidylserine | 1.00 (%) |
| Oil and fat | proper quantity |
| Sodium hydroxide | proper quantity |
| Sodium chloride | proper quantity |
| Flavoring | small quantity |

A total amount was to be 100 with purified water. A soap was manufactured with the compounding ratio.

| Formulation example 2: Lotion | |
| --- | --- |
| Phosphatidylserine | 3.00 (%) |
| L-ascorbic acid-2-magnesium phosphate | 1.00 |
| Water-soluble collagen (1% aqueous solution) | 1.00 |
| Sodium citric acid | 0.10 |
| Citric acid | 0.05 |
| Extract of licorice | 0.20 |
| 1,3-butylene glycol | 3.00 |
| Oil and fat | 2.00 |
| Serine | 1.00 |

A total amount was to be 100 with purified water. A lotion was manufactured with the compounding ratio (%).

| Formulation example 3: Cream | |
| --- | --- |
| Phosphatidylserine | 1.00 (%) |
| Polyethylene glycol mono stearate | 2.00 |
| Self emulsifying mono stearic acid glycerin | 5.00 |
| Cetyl alcohol | 4.00 |
| Squalene | 6.00 |
| Tri2-ethyl hexanoic acid glyceryl | 6.00 |
| Sphingoglycolipid | 1.00 |
| 1,3-butylene glycol | 7.00 |
| Vitamin C | 1.00 |

A total amount was to be 100 with purified water. A cream was manufactured with the compounding ratio (%).

| Formulation example 4: Pack | |
| --- | --- |
| Phosphatidylserine | 5.00 (%) |
| Polyvinyl alcohol | 13.00 |
| L-ascorbic acid-2-magnesium phosphate | 1.00 |
| Lauroylhydroxyproline | 1.00 |
| Water-soluble collagen (1% aqueous solution) | 2.00 |
| 1,3-butylene glycol | 3.00 |
| Ethanol | 5.00 |
| Serine | 1.00 |

A total amount was to be 100 with purified water. A pack was manufactured with the compounding ratio (%).

| Formulation example 5: Cosmetic solution | |
| --- | --- |
| Phosphatidylserine | 2.00 (%) |
| Hydroxyethylene cellulose (2% aqueous solution) | 12.00 |
| Xanthan gum (2% aqueous solution) | 1.00 |
| 1,3-butylene glycol | 6.00 |
| Concentrated glycerin | 4.00 |
| Sodium hyaluronic acid (1% aqueous solution) | 5.00 |
| Oil and fat | 2.00 |
| Serine | 1.00 |
| Vitamin C | 1.00 |

A total amount was to be 100 with purified water. A cosmetic solution was manufactured with the compounding ratio (%).

| Formulation example 6: Powders | |
| --- | --- |
| Phosphatidylserine | 100 mg |
| Lactose | 100 mg |
| Talc | 10 mg |
| Oil and fat | 5 mg |

The above ingredients were mixed and filled in the air-tight bag to manufacture powders.

| Formulation example 7: Tablet | |
| --- | --- |
| Phosphatidylserine | 50 mg |
| Corn starch | 100 mg |
| Lactose | 100 mg |
| Stearic acid magnesium | 2 mg |
| Vitamin C | 50 mg |

The above ingredients were mixed and tableted according to a typical tablet manufacturing method to manufacture a tablet.

| Formulation example 8: Capsule | |
| --- | --- |
| Phosphatidylserine | 50 mg |
| Corn starch | 100 mg |
| Lactose | 100 mg |
| Stearic acid magnesium | 2 mg |
| Vitamin C | 50 mg |
| Serine | 50 mg |

The above ingredients were mixed and filled in a gelatin capsule according to a typical capsule manufacturing method to manufacture a capsule.

| Formulation example 9: Injection | |
|---|---|
| Phosphatidylserine | 50 mg |
| Sterilized distilled water for injection | proper quantity |
| pH modifier | proper quantity |

The injection was manufactured with the above ingredient contents per ampoule (2 ml) according to a typical injection manufacturing method.

| Formulation example 10: Liquid formulation | |
|---|---|
| Phosphatidylserine | 100 mg |
| Glucose isomerase | 10 g |
| Mannitol | 5 g |
| Vitamin C | 50 mg |
| Serine | 50 mg |
| Oil and fat | proper quantity |
| Purified water | proper quantity |

According to a typical liquid formulation manufacturing method, each of the ingredients was added and dissolved in the purified water and lemon perfume was dropped in a proper quantity. The ingredients were mixed and then purified water was added so that a total amount is to be 100 ml. The overall solution was filled in a brown bottle and sterilized, thereby preparing a liquid formulation.

| Formulation example 11: Health food | |
|---|---|
| Phosphatidylserine | 1000 mg |
| Vitamin mixture | |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinic acid | 1.7 mg |
| Folic acid | 50 μg |
| Pantothenic acid | 0.5 mg |
| Inorganic mixture | |
| Ferrous sulfate | 1.75 mg |
| Zinc oxide | 0.82 mg |
| Magnesium carbonate | 25.3 mg |
| Potassium Phosphate Monobasic | 15 mg |
| Calcium phosphate dibasic | 55 mg |
| Potassium citrate | 90 mg |
| Calcium carbonate | 100 mg |
| Magnesium chloride | 24.8 mg |

Although the vitamins and mineral mixture were mixed and compounded according to a preferred embodiment relatively suitable for a health food, the compounding ratio may be arbitrarily modified. In addition, the ingredients may be mixed in accordance with a typical method to manufacture granules and then used for a health food composition manufacturing according to a typical method.

| Formulation example 12: Health beverage | |
|---|---|
| Phosphatidylserine | 1000 mg |
| Citric acid | 1000 mg |
| Oligosaccharide | 100 g |
| Plum concentrated solution | 2 g |
| Taurine | 1 g |
| Total amount by addition of purified water | 900 ml |

According to a typical health beverage manufacturing method, the ingredients were mixed and stirred and heated at 85° C. for about one hour. The obtained solution was filtered, poured into a 2 l sterilized vessel, seal-sterilized and kept in cold storage. Then, the solution was used to manufacture a health beverage composition.

Although the ingredients were mixed and compounded according to a preferred embodiment relatively suitable for a taste beverage, the compounding ratio may be arbitrarily modified in accordance with regional or national preferences such as demand classes, demand countries, uses and the like.

INDUSTRIAL APPLICABILITY

As described above, according to the invention, since the phosphatidylserine activates the PPAR-a of the tissue cell in the skin, the phosphatidylserine containing composition has effects of suppressing and alleviating the inflammatory response of the skin due to the skin external stimulation, reinforcing the skin barrier function to treat and improve the atopic skin having a weak skin barrier function, activating the PPAR-a of the tissue cell in the skin to promote a differentiation of the skin keratinocyte, protecting the skin keratinocyte from the ultraviolet irradiation or reactive oxygen species to promote the differentiation of the skin and to protect the skin, and preventing and improving the skin aging and wrinkles due to the ultraviolet. Accordingly, it is possible to protect and improve the skin from the injury due to the ultraviolet or the external stimulating material such as chemical material and to reinforce and strengthen the skin barrier function using the composition, thereby improving a general skin state.

The invention claimed is:

1. A method for protecting and improving a skin barrier function of a subject having an atopic skin,
    comprising administering to the subject an effective amount of phosphatidylserine that protects and improves skin barrier function in the subject,
    wherein the phosphatidylserine activates PPAR-alpha to promote the differentiation of skin keratinocytes in the subject, to suppress and alleviate an inflammatory response due to an external stimulation of the subject's skin, and
    the phosphatidylserine improves said atopic skin.

2. The method according to claim 1, wherein the phosphatidylserine is extracted from vegetable originated lecithin, animal oil and fat or manufactured by a phospholipase D transition reaction with the extracted lecithin or hydrogenated type phosphatidylserine.

3. The method of claim 2, wherein the vegetable originated lecithin is derived from soybean, corn, or mixtures thereof.

4. The method of claim 2, wherein the animal oil and fat is derived from egg yolk, milk, fish oil, a brain of an animal, or mixtures thereof.

5. The method according to claim 1, wherein the phosphatidylserine is transcutaneously or orally administered.

6. A method for suppressing and alleviating an inflammatory response of a subject having an atopic skin,
    comprising administering to the subject an effective amount of phosphatidylserine that suppresses and alleviates inflammatory response in the subject, wherein the phosphatidylserine activates PPAR-alpha to promote the differentiation of skin keratinocytes in the subject, to suppress and alleviate an inflammatory response due to an external stimulation of the subject's skin, and the phosphatidylserine improves said atopic skin.

7. The method according to claim 6, wherein the phosphatidylserine is extracted from vegetable originated lecithin, animal oil and fat or manufactured by a phospholipase D transition reaction with the extracted lecithin or hydrogenated type phosphatidylserine.

8. The method of claim 7, wherein the vegetable originated lecithin is derived from soybean, corn, or mixtures thereof.

9. The method of claim 7, wherein the animal oil and fat is derived from egg yolk, milk, fish oil, a brain of an animal, or mixtures thereof.

10. The method according to claim 6, wherein the phosphatidylserine is transcutaneously or orally administered.

11. A method for promoting skin differentiation or protecting skin from ultraviolet irradiation or reactive oxygen species of a subject having an atopic skin, comprising administering to the subject an effective amount of phosphatidylserine that promotes skin differentiation or protects skin from ultraviolet irradiation or reactive oxygen species in the subject, wherein the phosphatidylserine activates PPAR-alpha to promote the differentiation of skin keratinocytes in the subject, to suppress and alleviate an inflammatory response due to an external stimulation of the subject's skin, and the phosphatidylserine improves said atopic skin.

12. The method according to claim 11, wherein the phosphatidylserine is extracted from vegetable originated lecithin, animal oil and fat or manufactured by a phospholipase D transition reaction with the extracted lecithin or hydrogenated type phosphatidylserine.

13. The method of claim 12, wherein the vegetable originated lecithin is derived from soybean, corn, or mixtures thereof.

14. The method of claim 12, wherein the animal oil and fat is derived from egg yolk, milk, fish oil, a brain of an animal, or mixtures thereof.

15. The method according to claim 11, wherein the phosphatidylserine is transcutaneously or orally administered.

16. A method for treating skin aging and wrinkle due to ultraviolet irradiation or exposure of a subject having an atopic skin, comprising administering to the subject an effective amount of phosphatidylserine that treats skin aging and wrinkle due to ultraviolet irradiation or exposure in the subject, wherein the phosphatidylserine activates PPAR-alpha to promote the differentiation of skin keratinocytes in the subject, to suppress and alleviate an inflammatory response due to an external stimulation of the subject's skin, and the phosphatidylserine improves said atopic skin.

17. The method according to claim 16, wherein the phosphatidylserine is extracted from vegetable originated lecithin, animal oil and fat or manufactured by a phospholipase D transition reaction with the extracted lecithin or hydrogenated type phosphatidylserine.

18. The method of claim 17, wherein the vegetable originated lecithin is derived from soybean, corn, or mixtures thereof.

19. The method of claim 17, wherein the animal oil and fat is derived from egg yolk, milk, fish oil, a brain of an animal, or mixtures thereof.

20. The method according to claim 16, wherein the phosphatidylserine is transcutaneously or orally administered.

* * * * *